(12) United States Patent
Duckett, III

(10) Patent No.: US 11,307,430 B2
(45) Date of Patent: Apr. 19, 2022

(54) OPTICAL DEVICE AND METHOD FOR PROVIDING IMPROVED DEPTH OF FIELD AND RESOLUTION MODES

(71) Applicants: KARL STORZ SE & Co. KG, Tuttlingen (DE); KARL STORZ Imaging, Inc., Goleta, CA (US)

(72) Inventor: George E. Duckett, III, Castaic, CA (US)

(73) Assignees: KARL STORZ SE & Co. KG, Tuttlingen (DE); KARL STORZ Imaging, Inc., Goleta, CA (US)

(*) Notice: Subject to any disclaimer, the term of this patent is extended or adjusted under 35 U.S.C. 154(b) by 282 days.

(21) Appl. No.: 16/402,048

(22) Filed: May 2, 2019

(65) Prior Publication Data
US 2019/0265490 A1 Aug. 29, 2019

Related U.S. Application Data

(63) Continuation-in-part of application No. 15/175,520, filed on Jun. 7, 2016, now Pat. No. 10,324,300.

(51) Int. Cl.
*G02B 27/10* (2006.01)
*H04N 5/225* (2006.01)
(Continued)

(52) U.S. Cl.
CPC ...... *G02B 27/1066* (2013.01); *A61B 1/00009* (2013.01); *A61B 1/0019* (2013.01);
(Continued)

(58) Field of Classification Search
None
See application file for complete search history.

(56) References Cited

U.S. PATENT DOCUMENTS 4,801,792 A   1/1989   Yamasita
5,608,451 A * 3/1997   Konno ................. A61B 1/042
                                                     348/69
(Continued)

FOREIGN PATENT DOCUMENTS

EP   0602923 A1   6/1994
EP   2868254 A1   5/2015
(Continued)

OTHER PUBLICATIONS

Machine language translation of JP 2003-078802-A, Mar. 2003.*
(Continued)

*Primary Examiner* — John P Leubecker
(74) *Attorney, Agent, or Firm* — Michael J. Loi; David N. Villalpando

(57) ABSTRACT

An optical device, generally a camera head connected to an endoscope, provides multiple modes of operation, producing images with varying depth of field and/or resolution characteristics. Light from the endoscope passes through a variable aperture and a beam splitter and is directed to two or more independent image sensors. The image sensors may be moved, relative to each other, along their optical paths. An image processor combines the collected images into a resultant image. Adjustment of the relative positions of the image sensor and/or the diameter of the variable aperture permits the selection of optical properties desired, with a larger depth of field, and/or higher resolution than possible with a conventional system. Images may be collected through multiple acquisition periods, and a further enhanced image may be generated therefrom. The camera head may automatically make adjustments based on identifiers of the optical configuration of the attached endoscope.

24 Claims, 14 Drawing Sheets

(51) Int. Cl.
*A61B 1/04* (2006.01)
*A61B 1/00* (2006.01)
*G02B 27/28* (2006.01)
*H04N 5/232* (2006.01)
*G02B 23/24* (2006.01)

(52) U.S. Cl.
CPC ...... *A61B 1/00059* (2013.01); *A61B 1/00105* (2013.01); *A61B 1/00163* (2013.01); *A61B 1/00186* (2013.01); *A61B 1/00188* (2013.01); *A61B 1/042* (2013.01); *G02B 23/2453* (2013.01); *G02B 27/283* (2013.01); *H04N 5/2254* (2013.01); *H04N 5/2258* (2013.01); *H04N 5/23232* (2013.01); *H04N 2005/2255* (2013.01)

(56) References Cited

U.S. PATENT DOCUMENTS

| | | | |
|---|---|---|---|
| 5,793,539 | A | 8/1998 | Konno |
| 5,879,284 | A * | 3/1999 | Tsujita .................. A61B 1/043 600/109 |
| 5,944,655 | A | 8/1999 | Becker |
| 6,880,943 | B2 | 4/2005 | Fiete |
| 6,924,935 | B2 | 8/2005 | Miller |
| 6,943,946 | B2 | 9/2005 | Fiete |
| 8,784,301 | B2 | 7/2014 | McDowall |
| 8,878,919 | B2 | 11/2014 | Tsuyuki |
| 8,988,516 | B2 | 3/2015 | Sasamoto |
| 8,994,802 | B2 | 5/2015 | Suga |
| 9,030,543 | B2 | 5/2015 | Tsuyuki |
| 2001/0022687 | A1 | 9/2001 | Takahashi |
| 2002/0051070 | A1 * | 5/2002 | Ortyn .................. G02B 27/126 348/335 |
| 2003/0202252 | A1 * | 10/2003 | Beatson ............. G02B 27/1066 359/634 |
| 2006/0291844 | A1 * | 12/2006 | Kakkori .................. G03B 9/28 396/89 |
| 2007/0156021 | A1 | 7/2007 | Morse |
| 2007/0182844 | A1 * | 8/2007 | Allman ............ H04N 5/232122 348/345 |
| 2008/0079897 | A1 | 4/2008 | Goldfain |
| 2009/0076329 | A1 | 3/2009 | Su |
| 2010/0157019 | A1 | 6/2010 | Schwotzer |
| 2013/0083386 | A1 * | 4/2013 | Harding ............. A61B 1/00186 359/240 |
| 2014/0085421 | A1 | 3/2014 | Kuth |
| 2014/0176692 | A1 | 6/2014 | Tsuyuki |
| 2014/0198194 | A1 | 7/2014 | Suga |
| 2014/0300798 | A1 * | 10/2014 | Sapir .................. G02B 27/0075 348/345 |
| 2015/0309284 | A1 * | 10/2015 | Kagawa ............... G02B 27/126 348/76 |
| 2016/0157722 | A1 * | 6/2016 | Kubo .................... G06T 19/006 600/476 |
| 2017/0086657 | A1 * | 3/2017 | Bodor ................ A61B 1/00114 |

FOREIGN PATENT DOCUMENTS

| | | |
|---|---|---|
| EP | 2891448 A1 | 8/2015 |
| EP | 2375967 B1 | 8/2016 |
| JP | 06342122 A * | 12/1994 |
| JP | 2003078802 A * | 3/2003 |
| JP | 2006242976 A | 9/2006 |
| JP | 4226235 B2 | 3/2014 |
| WO | 2013025530 A1 | 2/2013 |

OTHER PUBLICATIONS

Mertens, et al., "Exposure Fusion," Computer Graphics and Applications, 2007, pp. 1-9.

Burt, P. J., and E. H. Adelson, "A Multiresolution Spline with Application to Image Mosaics," ACM Trans. on Graphics, 1983, vol. 2, No. 4, pp. 217-236.

Sufi, A., "Combining Exposure and Focus Fusion," Technical Paper Presentation, 2010, pp. 1-31, Rutgers University, New Brunswick.

Mcalpine, K., "A better 3D Camera with Clear, Graphene Light Detectors," University of Michigan News, 2016, pp. 1-3, Ann Arbor.

Fischer, M., Extended European Search Report for European Application No. 17000897.3, dated Oct. 4, 2017, pp. 1-7, Munich, Germany.

* cited by examiner a)

b)

OPTICAL DEVICE AND METHOD FOR PROVIDING IMPROVED DEPTH OF FIELD AND RESOLUTION MODES

CROSS-REFERENCE TO RELATED APPLICATION

This application is a continuation-in-part of U.S. application Ser. No. 15/175,520, filed on Jun. 7, 2016, and issued on Jun. 18, 2019 as U.S. Pat. No. 10,324,300 B2, entitled "Endoscope and imaging arrangement providing depth of field," that is hereby incorporated by reference.

BACKGROUND OF THE INVENTION

Field of the Invention

The presently disclosed device is directed to an optical system, generally in the form of a camera head used in conjunction with an endoscope, capable of producing views with increased depth of field, improved dynamic range, and/or enhanced resolution modes. The optical system utilizes a variety of beam splitters and beam-shapers to provide separate imaging channels to separate sensors.

Description of the Background Art

Conventionally, endoscopes were monocular, providing images through long telescoping lens arrangements. Initially, they allowed doctors to view, with their eyes, inside a patient. These relatively simple devices relayed images but did not provide depth information. As video-assisted surgery progressed, depth and size information was increasingly necessary, particularly, for tumor and thrombosis identification and assessment.

Some monocular endoscopes were modified to accept two perspective views of the same object and switch between each view, transmitting each one across a conventional single optical channel to a single sensor. The device described in U.S. Pat. No. 5,944,655 to Becker is exemplary. These devices provided stereoscopic views for doctors but required larger diameter distal tips to accommodate separate image capturing lenses, beam combiners and high-speed apertures. This made smaller overall diameter stereoscopic instruments difficult to produce.

Other devices were developed to provide an individual optical channel for each view and employed separate sensors in a mirrored configuration much like two side-by-side monocular endoscopes. This arrangement conserves distal tip volume at the expense of a thicker overall channel between the distal tip and the sensors. The device disclosed in US 2014/0085421 is exemplary of the state of the art.

Another endoscope arrangement is disclosed by Suga et al. in US 2014/0198194. This arrangement uses only a single image formation and transmittal channel, but splits the channel at the image sensing end. The embodiment disclosed in FIG. 1 of US 2014/0198194 is adapted to FIG. 1 of this disclosure. The polarizing beam splitting element 105, comprising two prisms 102, 103 near the distal end of the endoscope 101 divides the incoming captured light into two channels of differing polarization. The polarizing beam splitter 105 passes a first polarized beam through the interface between prisms 102 and 103. This first channel passes through the second prism 103 to a second interface and is reflected down to the sensor 107. The second channel consists of a differently polarized beam reflected upwards at the interface of the first prism 102 and transmitted through a $\lambda/4$ wave plate 104 before being reflected by a mirror 106 back through the $\lambda/4$ wave plate 104. The second channel beam, now having its polarization rotated by the two passes through the $\lambda/4$ wave plate 104, is transmitted through the beam splitting interface and falls upon the sensor 107. Each channel is separately focused due to path length differences within the prisms. These separate channels allow for a depth of field to be reconstructed from the two separately focused images. This endoscope, however, provides only static depth of field information, its optical elements all being fixed, thus, depth information is only be provided at two focal planes. This limits the amount of in-focus image information provided by the two images.

SUMMARY OF THE INVENTION

The invention disclosed herein relates to a dynamic imaging system for providing images of greater depth of field, and with higher resolution than has been possible heretofore. By providing for the adjustment of optical path length differences to expand a usable depth of field for an endoscope, while also enabling a variation in aperture size and/or shape to allow images of improved resolution to be captured by a plurality of sensors, a wide variety of modes of use for a given endoscope are now possible. The invention therefore provides improved versatility, allowing a particular mode to be selected, based on the preferences of the user and/or the requirements of the particular procedure being performed. Some embodiments of the optical device utilize a variable aperture to adjust the depth of field against the optimal image resolution, and one or more actuated sensors adjust the focal planes of one image sensor, providing a variation in detected focal planes. The imaging system is thus capable of capturing and adjusting the focal plane, the depth of field, and the resolution of separate images captured on separate sensors. In addition, certain embodiments enable other further modes of operation, including high dynamic range (HDR) imaging. An extensive variety of new modes of operation are thus made available to the user.

The imaging system can be designed for easy attachment to an endoscope. The optics are adapted to direct images to a number of sensors by splitting the incoming beam. Different beam splitter configurations can be provided to deliver two or more beams of variable optical path lengths to different sensors. These captured images with different focal planes, depths of field, and resolution require additional processing to generate a combined image, if so desired. Alternatively, the individual captured images may also be displayed with our without the processed image. Some example methods of image processing, as are known in the art, are presented below, however, the invention should not be considered limited to including the processing steps of these examples.

The image fusion methods of Mertens, et al. "Exposure Fusion" by Mertens, et al. in Computer Graphics and Applications (2007) and Burt, et al. "A Multiresolution Spline With Application to Image Mosaics" ACM Transactions on Graphics, Vol. 2. No. 4, October 1983, p. 217-236 are adapted to combine the differently focused images of the imaging system into one clearer image. The combination of these processes can handle focal variations (far and near) as well as exposure differences (over and under). First the fusion method generates a contrast weight map, a saturation weight map and an exposure weight map for each captured image. Second, these maps are applied to select the best pixels from each image. Finally, the separate weighted images containing the selected or weighted pixels are combined with pyramid-based image fusion. The journal article "Exposure Fusion" by Mertens, et al. in Computer Graphics and Applications (2007) is incorporated herein by reference. Likewise, Burt, et al. "A Multiresolution Spline With Application to Image Mosaics" ACM Transactions on Graphics, Vol. 2. No. 4, October 1983, p. 217-236 is incorporated herein by reference.

The imaging system is an element of an optical device such as a camera head for an endoscope, such that the camera head can be connected to a variety of endoscopes. In addition to beam splitting and any necessary image shaping optics, the camera head can include a Radio Frequency Identification (RFID) receiver, or other identifying means, for detecting the endoscope, aiding in the coupling procedure, and gathering any information necessary for the camera head to make appropriate adjustments to its optical elements, enable the various operational modes available to the user, and provide information about the endoscope to the image processor. Upon detection of the particular endoscope being used, the imaging system may adapt the sensor positions, aperture opening size and shape, and other optical elements as necessary to utilize the light beam transmitted from the particular attached endoscope. Alternatively, the imaging system can be an element of a single instrument, that is, one instrument comprising an endoscope and non-detachable camera head.

Further scope of applicability of the present invention will become apparent from the detailed description given hereinafter. However, it should be understood that the detailed description and specific examples, while indicating preferred embodiments of the invention, are given by way of illustration only, as various changes, combinations, and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention. The index numbers used throughout attempt to convey uniformity as much as possible, while also permitting distinct reference thereto. Therefore, the numbering system employed is for the sake of simplicity and clarity and should not be considered limiting.

FIG. 6a shows one embodiment of the polarized variable aperture, and FIG. 6b illustrates the aperture as an element of the inventive optical system.

FIG. 13 describes an example mode of the present invention according to FIG. 5 where two high-resolution, narrow depth of field regions are produced with an out-of-focus region there between.

DETAILED DESCRIPTION

Conventional methods to increase depth of field fundamentally decrease the resolution. Thus, typically systems are forced to make a tradeoff between depth of field and resolution. Above referenced co-pending U.S. application Ser. No. 15/175,520 discusses, in detail, various means by which the depth of field of a given scene can be increased by combining data from several image sensors to provide increased depth information. Some of the embodiments presented therein, as well as those of the present disclosure, permit the preservation of resolution as well as, even, the ability to improve it. Further, the present invention enables the selection of various modes of operation, increasing thereby, the versatility of any appropriate endoscope used with the inventive optical system. Images collected on a plurality of sensors and/or over multiple acquisition periods can be processed to provide the in-focus portion of each captured image for a clearer image with more depth information and increased depth of field. In particular, the present invention enables the collection of narrow-depth of field, high resolution images in addition to lower resolution, deep depth of field images to provide enhanced images for a variety of applications.

Figure 1:
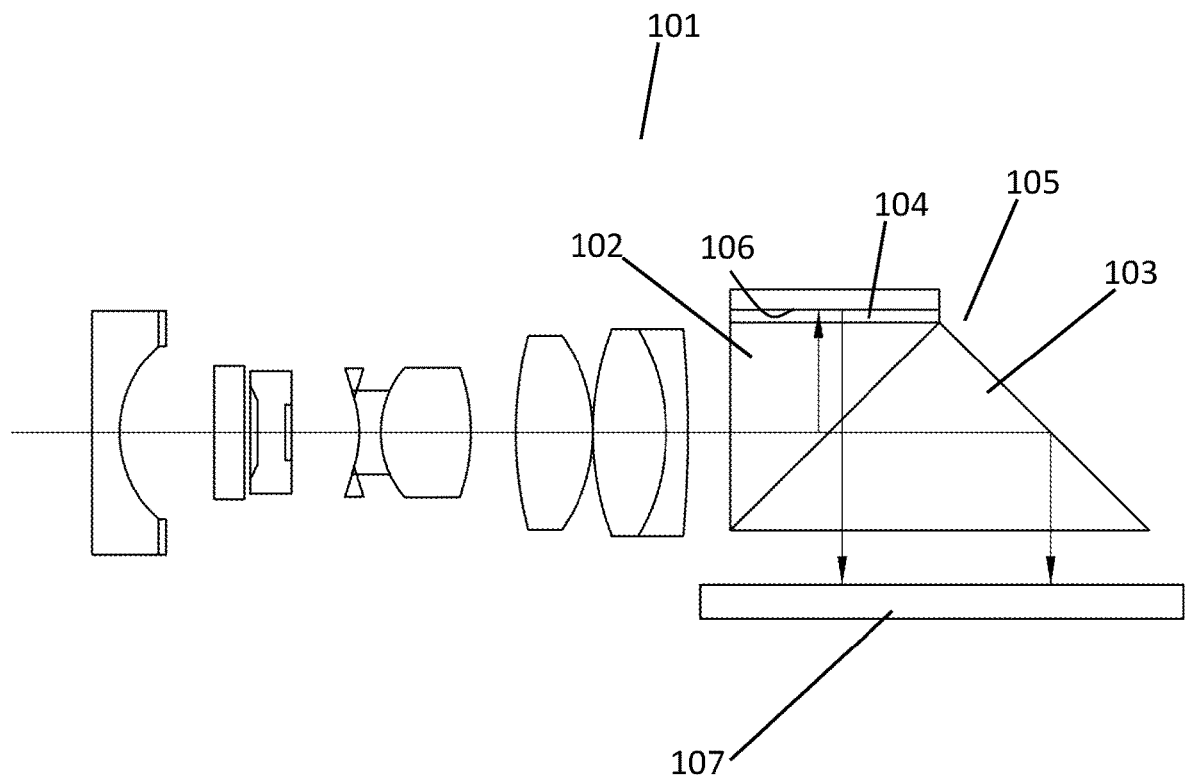
FIG. 1 illustrates a prior art optical system for providing an extended-depth of field to the view of an endoscope.
Figure 2:
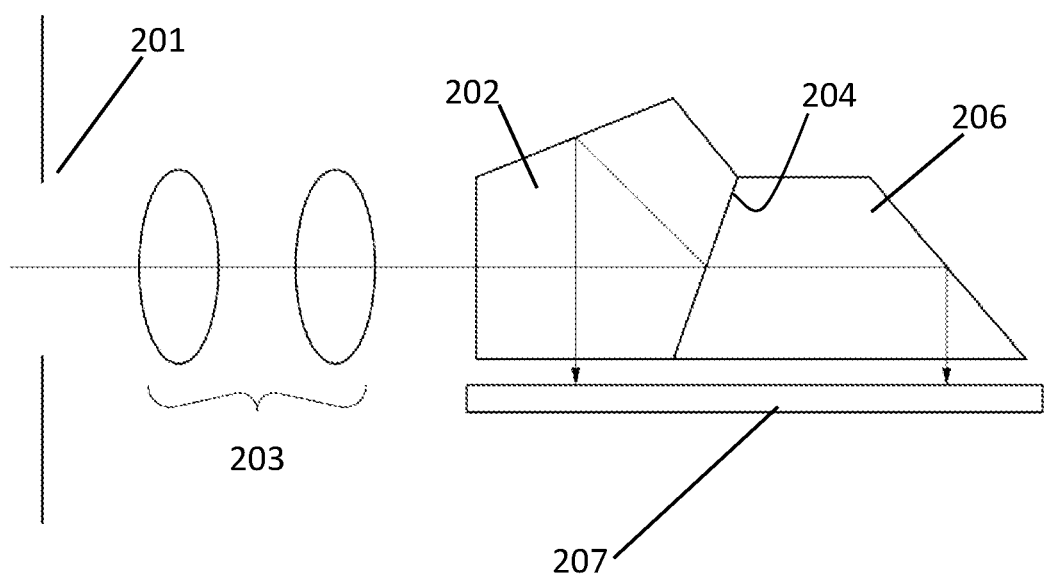
FIG. 2 shows an example optical system including a pentaprism for capturing two versions of the same image with varying focal planes.

One means for providing an image with a wider depth of field than is conventionally possible is with the fixed aperture system shown in FIG. 2. A beam of light passes from an attached endoscope through a fixed aperture 201 from a carrier lens 203. The size of the aperture determines the maximum resolution of a detected image. In general, the smaller the aperture, the larger the depth of field, but the lower the resolution. In this example, the beam from the carrier lens enters the pentaprism 202 and is partially reflected off a first interface 204 and then internally reflected back towards a sensor 207. The remaining light passing through the interface is reflected off a back surface of a second prism 206 towards the same sensor 207. The first interface 204 can be a half-silvered mirror or semi-reflective coating on one of the prism surfaces. Each reflection changes the path length and, as a result, the back focal length of each beam is different. The image formed on each portion of the sensor 207 therefore captures a separate focal plane of the object being observed by the endoscope. The separately captured images can then be segmented and recombined to provide a resulting image with a larger depth of field, that is, with a longer in-focus range, than would be possible with a similar system having only one image sensor capturing light with a single optical path length. It should also be noted, however, that this system allows the use of a larger diameter aperture 201 for incoming light than would have been possible in a conventional system to achieve the same depth-of-field, resulting in a higher resolution. An alternative arrangement might include two separate sensors in place of the single sensor 207. The individual sensors could be placed at different distances from the beam splitter, providing greater versatility of design to meet specific needs.

Figure 3:
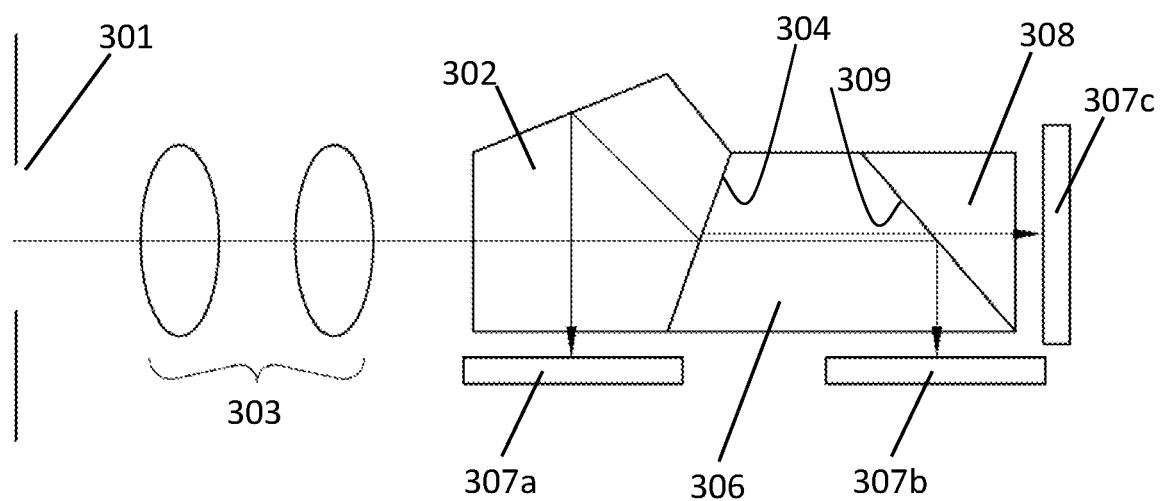
FIG. 3 shows an example optical system similar to FIG. 2 where three versions of the same image are captured with three distinct focal planes.

Another illustrative design is shown in FIG. 3. The beam splitter of this embodiment includes a beam splitter similar to that of FIG. 2 along with an additional rear prism 308. This arrangement further splits the remaining light passing through the interface 309. The interface 304 can be ⅓ reflective and interface 309, 50% reflective and the sensors 307, individually detecting each partial beam, can be offset from the prisms at different distances. The additional interface 309 providing for a third beam to be captured by a third sensor 307*c* for additional depth of field information. Each separate sensor 307 detects a differently focused beam providing an image including information at a particular depth. Each of the beam splitter elements or prisms (302, 306 and 308), can be made of crystal glass, polymers, acrylic, or other light transmitting materials. Also, the interfaces (304, 309) can be made partially reflective such that the intensity of each sensed beam is substantially equal. Alternatively, to compensate for surface losses or other differences, the reflective surfaces on the interfaces (304, 309) may divide the beams unequally. Generally, the embodiments shown in FIG. 2 and FIG. 3 utilize a single, fixed aperture (201, 301), defining, thereby, a fixed depth of field for each detector. Therefore, these embodiments may be generally fabricated with pre-set values for depth of field and focal plane position for each corresponding detector. However, as will be discussed in greater detail in preferred embodiments below, it is not necessary that the aperture size (or shape), nor the positioning of the sensors, be fixed, permitting, thereby, the modes of operation discussed below.

Figure 4:
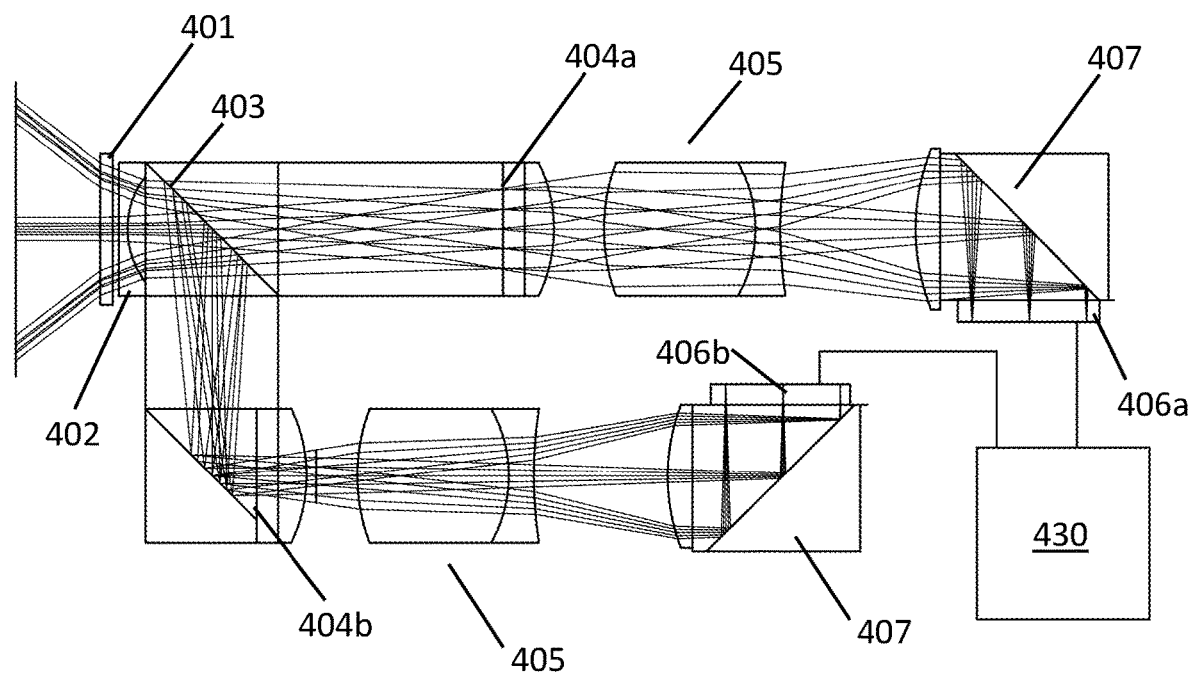
FIG. 4 illustrates an optical system with a plurality of aperture sizes and fixed focal planes.

An alternative arrangement for capturing images with varying depths of field/resolution is shown in FIG. 4. As with other structures presented herein, this embodiment, with simple variations to the optical design, known in the art, can take the form of either a camera head for use with a detachably connected endoscope or can be a distally placed optical device, generally referred to as a "distal tip endoscope." The embodiment of FIG. 4 shows a cover glass 401 and a beam shaping lens 402. The incoming light beam is split into two beams by a beam splitter 403. Each beam then passes through a corresponding individual aperture stop 404, each aperture stop 404*a*, 404*b* having a different diameter. The difference in diameters results in captured images with distinct depth of field and resolution characteristics. Each beam passes through carrier lenses 405 before being reflected by the respective mirrors 407 onto the sensors 406. Lenses can also be disposed immediately upstream of the mirrors 407 to differently focus the light beams so that the sensors 406 can be mounted directly to the mirror blocks 407 at equal distances. In this case, when apertures 404 are of fixed diameter, and when the optical path lengths traversed by the beams are equal, the sensors will record two images of the same focal plane. The beam having passed through the larger aperture, will produce an image with a narrower depth of field and a higher resolution, while the other sensor, its beam having passed through a more narrow aperture, will capture an image with a larger depth of field, but of lower resolution. Processing of the collected images by an image processing unit 430 can provide a final image with enhanced depth of field and resolution, over an image collected by either optical channel alone.

Further versatility can be added to this embodiment by incorporating variable apertures 404*a*, 404*b* to vary the depth of field and resolution of the captured images at a given focal plane from one acquisition period to the next. In addition movable or variable focus lenses can be placed within one or both of the optical channels to vary the path focal plane. Focal plane variation can also be achieved by moving one or both of the image sensors along the optical path, increasing the distance relative to the beam splitter 403. These variations can provide various modes of operation and/or can be used to capture multiple images over multiple acquisition periods, and processed to provide a resulting enhanced image.

Figure 5:
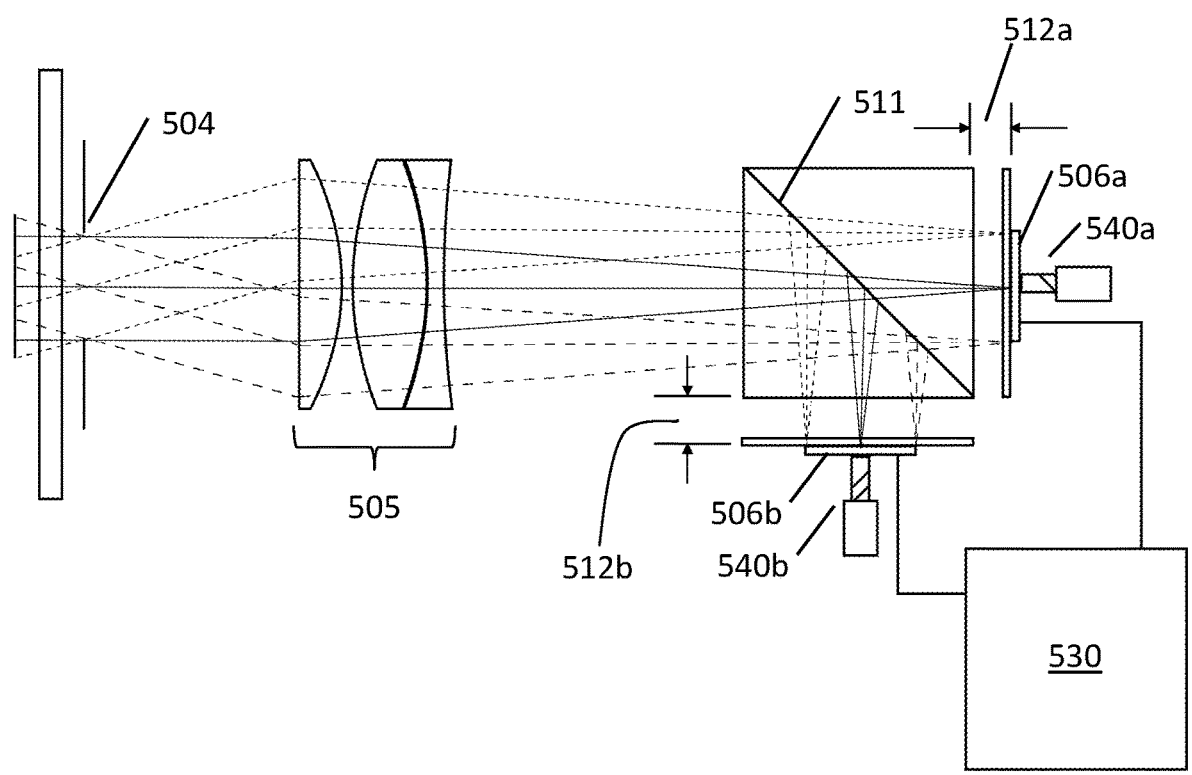
FIG. 5 shows an optical system with a variable aperture through which image light passes, is split and falls onto a plurality of movable image sensors.

A preferred embodiment of the present invention, and that which will be used to illustrate most of the inventive modes discussed below, is shown in FIG. 5, wherein incoming light from an endoscope (not shown) passes through a variable aperture stop 504 and focusing and shaping optics 505. The light beam is then split by beam splitter 511 and captured by sensors 506. Each sensor 506*a*, 506*b* may be offset from the beam splitter at different distances 512*a*, 512*b*, resulting in two focal planes being captured. In a most preferred embodiment, the aperture stop 504 is a variable aperture stop, and thus, in addition to the multiple modes enabled, additional depth of field and resolution information can be obtained when varied over multiple acquisition periods. In another preferred embodiment, one or more of the image sensors 506 can be connected to a corresponding small actuator 540 that can adjust the focal plane position, generally along the optical axis. The actuators 540 can be a piezo-electric motor or other small motor. This allows the focal plane difference seen by the two sensors to be adjusted for a particular situation or mode of operation. Further, the actuator can be used in conjunction with information received by an identifier such as an RFID identifier from an attached endoscope to optimize the combined system for a particular use. In addition these actuators can be used to position each detector in a factory default setting that can, through a calibration step, correct certain optic variations which may be present between one manufactured instrument and the next.

Figure 6:
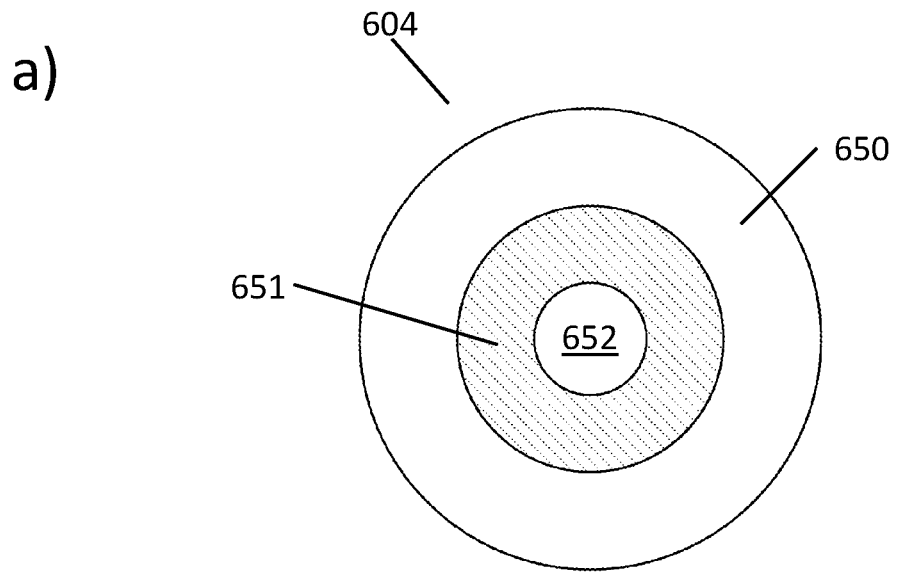
FIG. 6 shows an alternative variable aperture with an annular polarized region.
Figure 6:
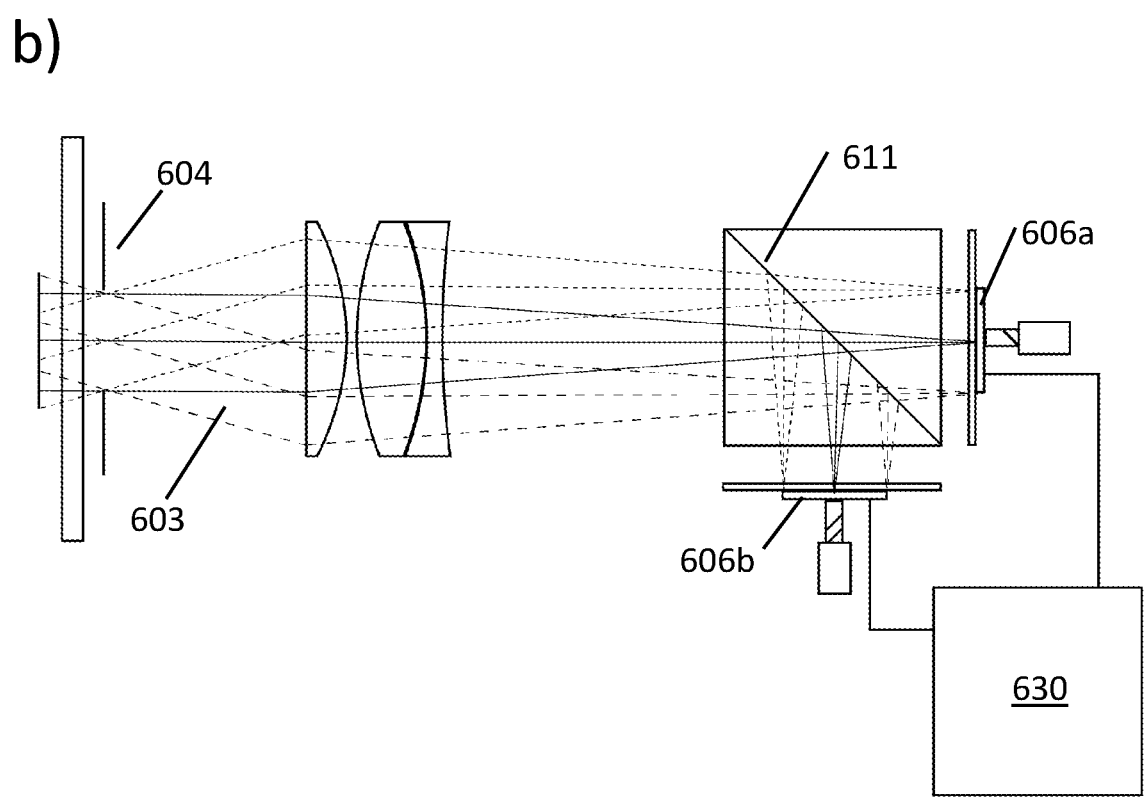

An alternative to a temporally variable aperture stop as discussed above in relation to the embodiment shown in FIG. 5, or that may be used in conjunction therewith, is the variably-polarized aperture stop shown in FIG. 6*a*. This specialized aperture stop 604 includes an outer opaque annular region 650, an inner polarizing annular filter 651, and an innermost circular opening 652 with no filter. This graduated aperture provides different f-numbers for beams of polarized and non-polarized light. A beam 603 exiting the aperture 604 is a separable beam including two overlapping beams propagating together, these beams are divided by a polarized beam splitter 611, replacing the conventional beam splitter 511 of FIG. 5. After separation, one beam has a higher f-number than the other beam. Thus, one beam can be imaged at high resolution and the other beam can be image at a high depth of field. A processing unit 630 can then generate a single image with a higher depth of field and/or higher resolution than would be possible with a single sensor and conventional optical arrangements. The effect can be increased if the sensors 606 are in different focal planes, and further modes of operation can be achieved by varying the distance of one or both of the image sensors relative to the beam splitter. Alternatively, the polarizing filter 651 may be instead a spectral filter, with the beam splitter 611, splitting rather by spectrum. In addition, more levels or annular regions within the graduated aperture of FIG. 6a may also be advantageous under certain circumstances. Further, a temporally variable aperture, as discussed above, may be used in conjunction with the annular polarizing aperture, wherein the size of the polarizing ring may be changed by a temporally variable aperture placed upstream or downstream from the annular polarizing aperture 604. In certain modes, the dual size aperture features may be disabled by stopping down the temporally variable aperture to the diameter, or below, of the polarizing, annular region, permitting, thereby, only a single, non-polarized beam to pass there through.

The many embodiments of the present invention generally comprise a control device for controlling a variable aperture and/or sensor positions, and a processor that performs the necessary image processing procedures that are known in the art, discussed only briefly here, including the calculation of depth from the captured images, the segmenting the in-focus portions of the images, and the recombination for display. The processor may also be able to model three-dimensional surfaces and build complex tissue models. These models and surfaces can be stored in memory such as RAM or transmitted to a display screen for display to a user. Digital image processing can combine each of the differently focused and differently resolved, separately captured images by selecting and extracting the sharp areas of each image and combining them into a single full resolution image. Additionally, the color information from blurred areas can be reconstructed using the contrast information of the sharp areas of the combined image such that the colors are accurately reproduced. First the fusion method generates a contrast weight map, a saturation weight map and an exposure weight map for each captured image. Then these maps are applied to select the best pixels from each image. Finally, the separate weighted images containing the selected or weighted pixels are combined with pyramid-based image fusion to generate a combined image. By interpolating the color information, both resolution and contrast are slightly reduced. This, however, should not be problematic as the resolution of the sensors and combined image generally exceeds the resolution of the best endoscopes. On the other hand, the increased depth of focus allows for certain errors in the optics such as image field curvature to be compensated. Image field curvature often occurs in endoscopes with a very long inversion system. Optimally, the ray bundles at the focal planes should be telecentric, such that the moving of the image sensors along the optical path will not change the size of the detected image circle. Non-telecentric ray bundles, however, can be corrected for with further image processing.

Figure 7:
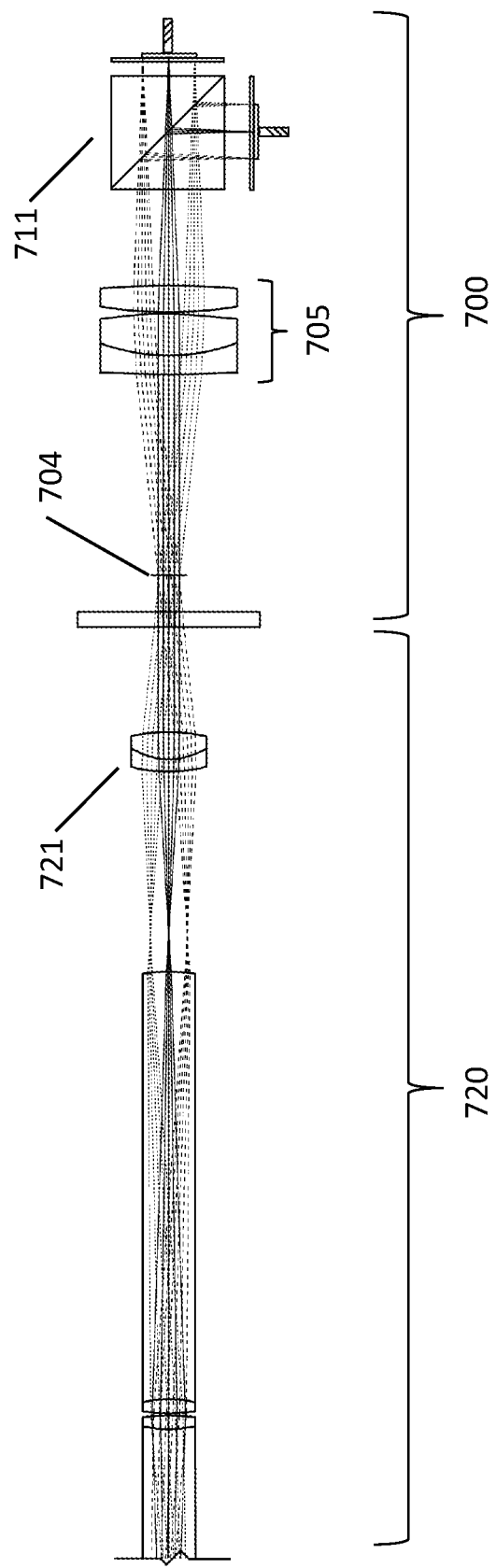
FIG. 7 shows the optical system of FIG. 5 in conjunction to a relay system of an attached endoscope.

The larger system diagram of FIG. 7 illustrates how any of the camera heads disclosed herein might interact with an endoscope optical head 720. In the illustrated case, the variable aperture 704 is placed upstream from a beam shaping lens group 705 used to control and adapt the light beam received from the endoscope, and further collimating lens groups may be placed downstream of the beam splitter 711 as necessary. The rod lens endoscope 720 could be any of a number of conventional endoscopes or ones specially adapted to identify with the disclosed camera head, and may include an ocular element 721 to appropriately condition the beam. The camera head portion 700, when used with an embodiment of the present invention utilizing a non-variable aperture, can include an aperture stop smaller than the exit pupil of the endoscope. As discussed previously, this would increase the depth of field but also reduce the resolution. Alternatively, the camera head could provide a fixed offset between focal planes. However, to provide a fixed offset across different endoscopes, the camera head would need to adjust to each endoscope type, and such adjustments could be trigged by detection of an identifier, such as an RFID, optical or other identifier, as discussed below. The camera head can be integrated into or detachable from a video-endoscope. The loss of light due to the distribution of the light beam onto various sensors may be compensated in that the system can have a higher numerical aperture than an equivalent system that covers the same depth of focus with a single sensor as this system does with multiple sensors. With the higher numerical aperture, overall a higher resolution is achieved. In conventional systems this high resolution requires lower depth of field as a trade-off.

Figure 8:
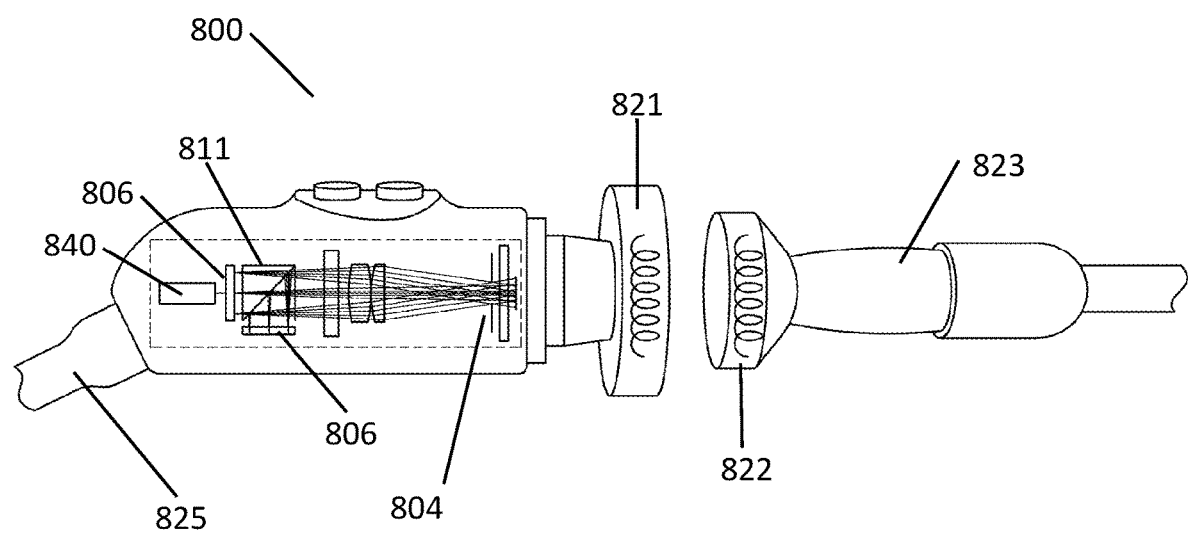
FIG. 8 illustrates an example optical device according to the present invention with an RFID receiver, receiving information from an RFID identifier contained in the endoscope.

The outlined device in FIG. 8 shows an exemplary camera head as an element of a handle 800 with a specialized Radio Frequency Identification (RFID) reader unit 821 for detecting an RFID identifier (or tag) 822 for a specific endoscope type 823. The camera head is surrounded by a handle structure 800 for easy handling by the operator. The digital signals from the sensors may then be sent via connecting line 825 (or another suitable means, such as a wireless communicator) to a processing unit or display unit. Alternatively, the digital processing of the sensor images can be performed in the handle element 800 with only a combined image being sent to the display or storage means. The camera head can identify the endoscope 823 being attached and store in memory or adjust automatically, based on a detection of a specific endoscope type, the optimal diameter of a variable aperture 804 and/or the positions of the sensors 806. In either case, the adjustment preferably optimizes any focal offset introduced by these elements. It should also be noted that in the example embodiment shown, only one sensor is capable of movement by connection to an actuator 840, however, neither the embodiment shown in FIG. 8, nor other embodiments should be considered limited to either requiring more than one, or restricted to only one, movable sensor. Depending on the restrictions (including space, cost, etc.) necessary for any given camera head, the proper number of movable sensors may be implemented, and any remaining sensors may be fixed.

Upon the identification of the specific endoscope 823 from the tag 822 on the proximal end of the endoscope, one or more of the actuators 840 adjusts the relative focal planes of the sensors 806 to an optimal focal plane offset. Alternatively, the identification can be done via the camera head with a QR code, bar code, or a specific color scheme on the endoscope end. Additionally, the endoscope could be identified by direct connection via a data bus or by analysis of electrical resistance or a magnetic field direction of the endoscope end.

The actuator 840 can be a piezo-electric motor or other small motor. Upon identification of the endoscope tag 822, a RFID reader 821 of a camera head 800 signals a controller for the variable aperture stop 804. The variable aperture stop 804 is preferably disposed before the beam splitter 811 for adjustment to a default depth of field setting. In addition, the controller could be linked to a variable liquid lens within the optical system.

It is also noted that any of the camera heads and optical arrangements disclosed herein may be implemented into the device of FIG. 8. The combined image from the several sensors of any of the camera heads will preferably be calculated in real time for an image with improved depth of field and increased resolution. If this is not possible, then a real time average value of the images super-imposed on each other can be generated with the calculated image being available later. In addition, three-dimensional modeling from the different focal planes can be calculated either in real time and displayed on a three-dimensional display or calculated and generated later for analysis and diagnosis.

Modes of Operation

We will now, with particular reference to FIGS. 9-14, turn to the modes of operation of the present invention that are enabled by the inventive camera heads described above. Throughout discussion of these various modes, reference will be made to the embodiment set forth in FIG. 5, but it should be noted that any of the inventive camera heads disclosed herein capable of enabling some or all of these inventive modes are part of the present invention.

As the embodiment of FIG. 5 includes the ability to vary both the depth of field of a captured image as well as to adjust the focal planes of each detector, while collecting differing images of the same object space simultaneously, a variable mode camera head that may be used with any number of endoscopes is enabled. Below are presented various exemplar modes of operation for this multi-mode optical device. Throughout the description of these modes, we will set forth example conditions such as "wide" or "narrow" aperture size, "narrow" or "deep" depth of field, etc. It should be understood that these terms are used as a matter of convenience to better explain the inventive modes enabled hereby, and are not intended to imply specific limitations or suggest that only these exemplar modes and/or settings define the invention; rather, any number of settings between each of these are elements of the invention.

FIGS. 9-14 demonstrate the various modes of operation with relation to a ruler seen in object space. It should be noted that these examples are presented only qualitatively, and are not meant to indicate any limitations regarding the optics of the system or actual depth and/or resolution values, and are presented for their descriptive qualities in order to better understand the invention.

Figure 9:
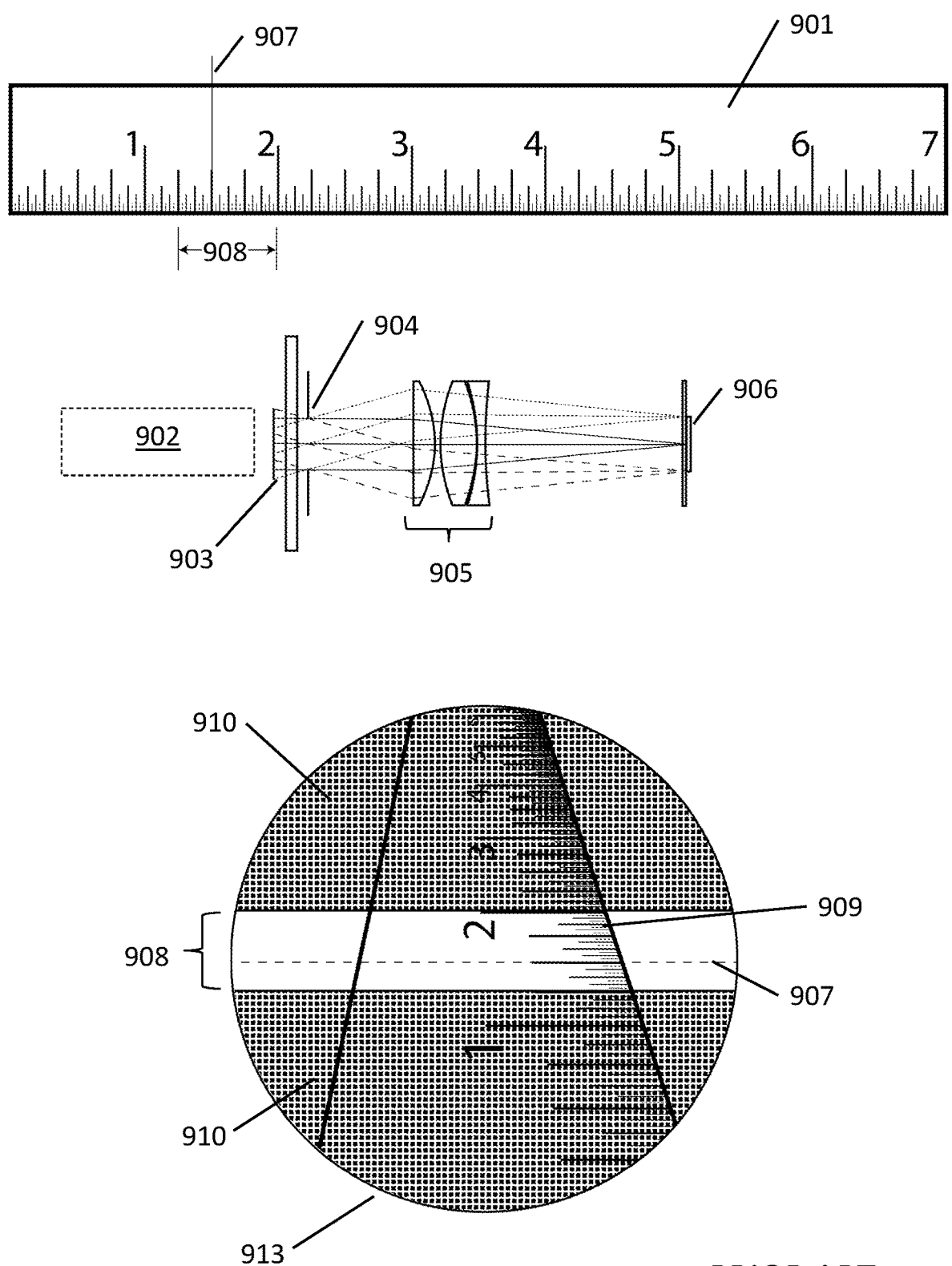
FIG. 9 illustrates a conventional endoscopic system yielding an image with a high resolution and narrow depth of field.
Figure 10:
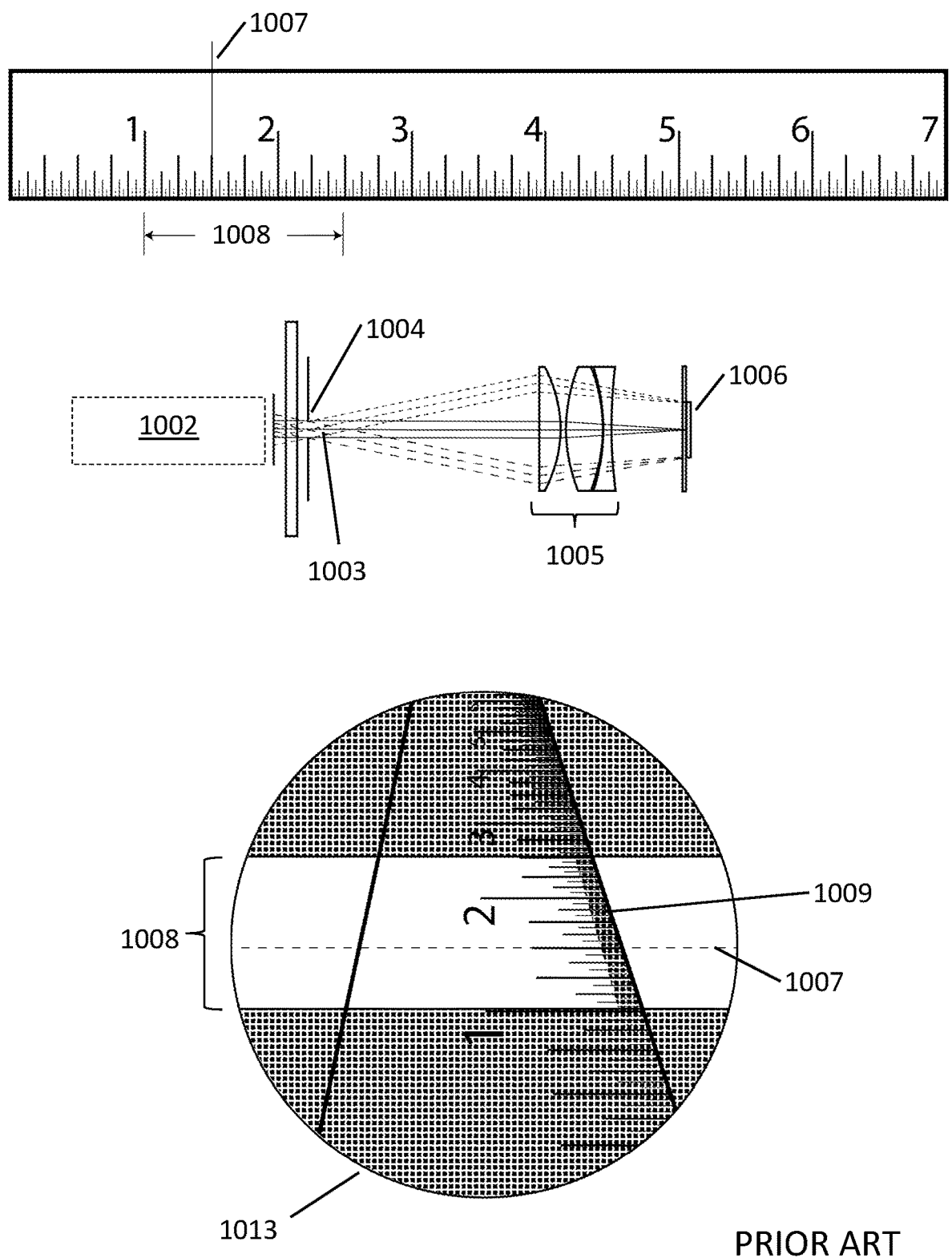
FIG. 10 illustrates a conventional endoscopic system yielding a lower resolution image with a wide depth of field.

FIGS. 9 and 10 illustrate two differing conditions possible with two separate conventional endoscopes. FIG. 9 shows the conditions where a narrow depth of field, but high resolution image is captured on a single sensor. The ruler 901 is in the object space seen by the endoscope 902. Light 903 collected by the endoscope passes through a fixed aperture 904 with a wide diameter, through the focusing optics 905 and on to be detected by image sensor 906. The resultant image has a fixed focal plane 907, and a depth of field 908, where the image is considered in-focus, that being the depth from the 1¼" mark to the 2" mark. The wide aperture 904 allows a high resolution image to be captured and displayed, as illustrated graphically by the ⅟₃₂" tick marks 909 being clearly resolved in endoscopic output 913. Outside of this depth of field region 908, however, the image becomes blurred as in regions 910.

By contrast FIG. 10 shows the conditions for a conventional endoscope 1002 with a wide depth of field, but with lower resolution. In this case, the aperture 1004 has a narrow diameter, permitting only a smaller beam 1003 there through, which passes through shaping optics 1005 to image sensor 1006. The captured image has a focal plane 1007 at the same position as in the example of FIG. 9, but it has a significantly wider depth of field 1008. Hence a region from the 1" mark to the 2½" mark is in focus. However, as discussed above, a practical trade-off for the wider depth of field is a lower resolution, and, as a result, the ⅟₃₂" marks 1009 are not clearly resolved, even in the in-focus region 1008 as seen in the output display 1013. Traditionally, these types of tradeoffs had to be made depending on the nature of the procedure to be performed, and a surgeon was required to select an appropriate instrument, resulting in the need to acquire any number of endoscopes as well as camera head elements to which they are attached to achieve the desired operating conditions.

Figure 11:
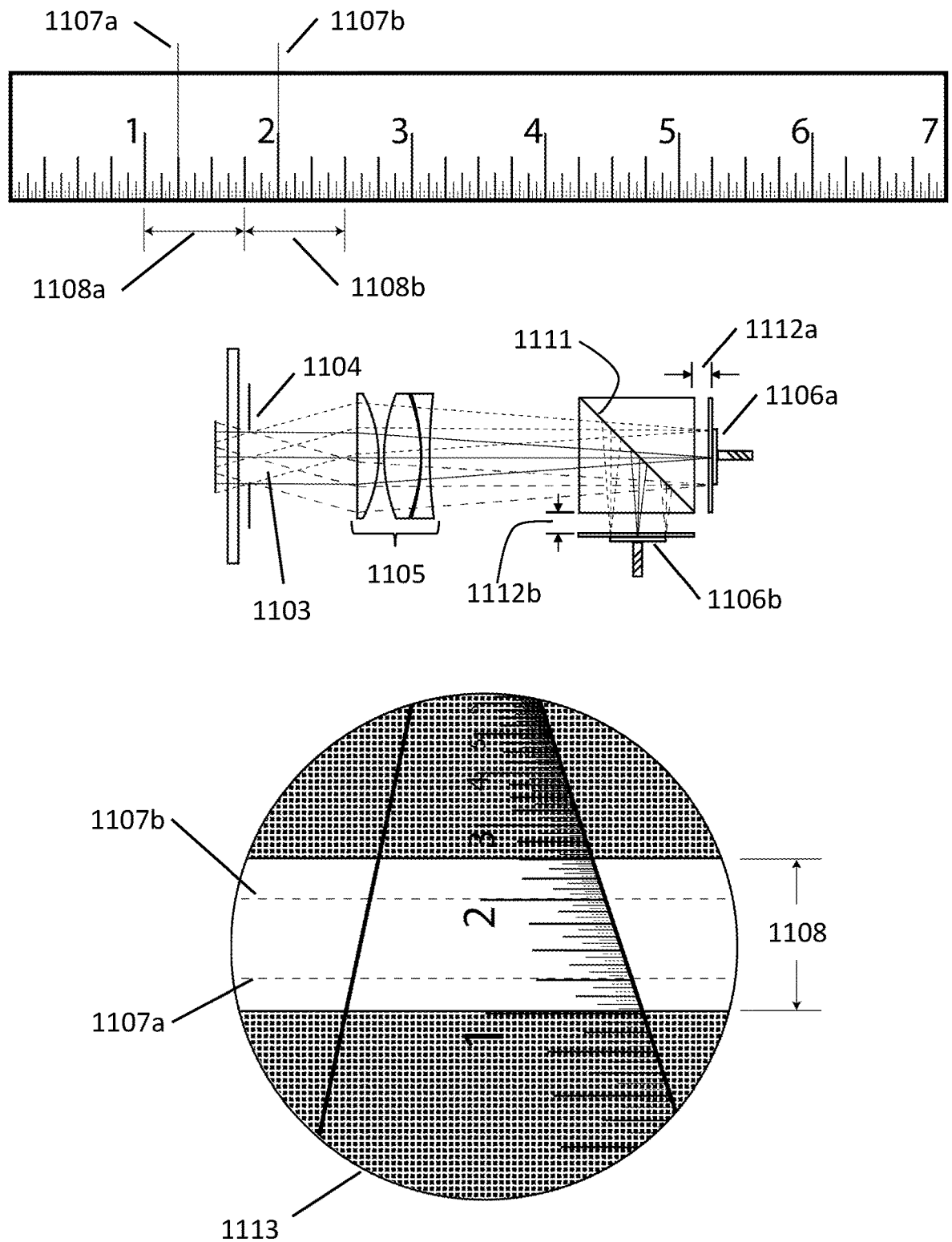
FIG. 11 illustrates an example mode of the present invention according to FIG. 5 yielding a high-resolution and extended depth of field image.

FIG. 11 illustrates an example embodiment of the present invention where in an extended depth of field/full resolution mode. As discussed above, this embodiment utilizes a variable aperture 1104. For this example mode of operation, this aperture 1104 is opened to a wide diameter, permitting thereby the passage of a wide beam 1103 through the shaping lenses 1105, and incident on beam splitter 1111. Sensors 1106a and 1106b are positioned such that their distances, 1112a and 1112b respectively, from the beam splitter 1111 are not equal, resulting in a different focal planes 1107a and 1107b being observed by the respective sensor. In this example mode, the distances 1112a and 1112b are selected such that the in-focus region determined by the depth of field 1108b about the focal plane 1107b seen by the second detector 1106b overlaps or abuts the in-focus region determined by the depth of field 1108a about the focal plane 1107a observed by the first detector 1106a. This enhanced resolution mode provides two high-resolution, in-focus regions to be captured on the individual sensors with a combined in-focus range 1108. A composite image 1113 is then created with a resolution equal to that possible in a conventional system with a similarly wide aperture (as represented by FIG. 9), but with a wider in-focus depth, as represented in the endoscopic view 1113, wherein the in-focus region spans from the 1" to the 2½" marks, and where the entire in-focus region is of high resolution, hence the ⅟₃₂" tick marks are clearly resolved.

It should be noted that the physical distances 1112a and 1112b of the sensors 1106a and 1106b (respectively) to the beamsplitter 1111 are, in reality not the critical element of determining the focal plane for each sensor, but, rather, it is the optical path length of the beam traveled that determines the detector's focal plane. Therefore it should not be considered limiting for this mode (or any other relevant mode) that distances 1112a and 1112b are actually unequal, but only that their positioning determines a differing focal plane. For example, it is possible that an element of the beam splitting prism contains a differing refractive index, or where one element of the prism is of a longer length than the other, resulting in a longer effective optical path length for one of the beams relative to the other, and in such a case, distance 1112a and 1112b could be equal, and still generate the present extended depth of field/full resolution mode. Therefore reference to distances of the sensors to the beam splitter are presented throughout this disclosure, primarily for the sake of simplicity, and should not be considered limiting insofar as it is the optical path length variation, not necessarily the distance from the beam splitter (or beam splitting prism) that is essential, as will be understood by those skilled in the art.

Figure 12:
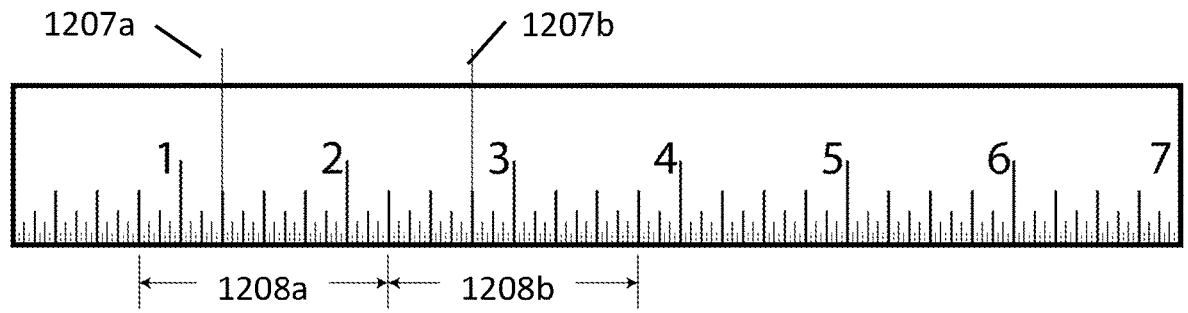
FIG. 12 illustrates an example mode of the present invention according to FIG. 5 yielding a standard resolution and further extended depth of field.
Figure 12:
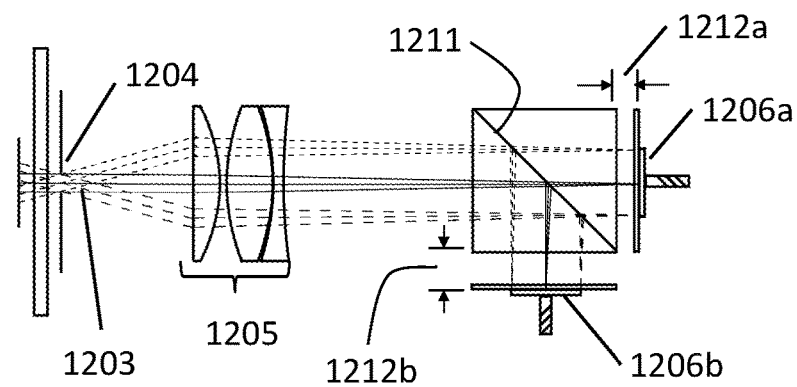
Figure 12:
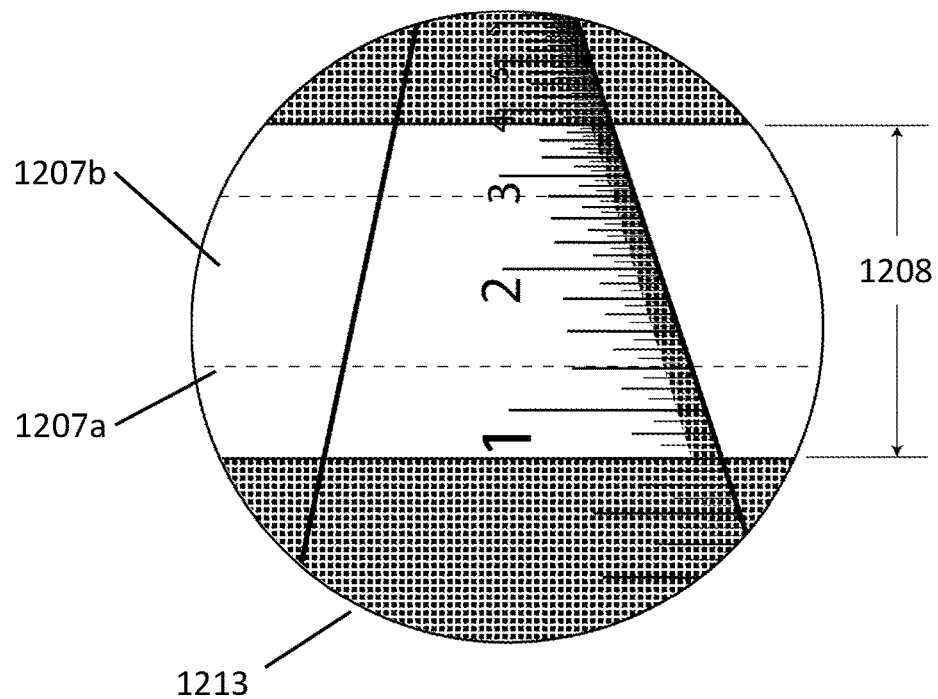

Another possible mode of operation is represented in FIG. 12. This extended depth of field mode is selected for illustration to contrast with the mode represented in FIG. 11. When this mode is selected, the variable aperture 1204 is stopped down to a narrow diameter, permitting thereby the passage of a narrow beam 1203 through the shaping lenses 1205, and incident on beam splitter 1211. Sensors 1206a and 1206b are positioned such that their distances, 1212a and 1212b respectively, from the beam splitter 1211 are not equal, resulting in different focal planes 1207a and 1207b being observed by the respective sensor. In this example mode, as in the previous, distances 1212a and 1212b are selected such that the in-focus region determined by the depth of field 1208b about the focal plane 1207b seen by the second detector 1206b overlaps or abuts the in-focus region determined by the depth of field 1208a about the focal plane 1207a observed by the first detector 1206a. This extended depth of field mode provides two lower-resolution, in-focus regions to be captured on the individual sensors, resulting in an overall larger in-focus region 1208. A composite image is then created with a resolution equal to that which would be possible in a conventional system with a similarly stopped down aperture (as represented by FIG. 10), but with a wider in-focus depth, as represented in the endoscopic view 1213 wherein a the in-focus region spans from the ¾" to the 3¾" inch marks, and where the entire in-focus region is of lower resolution, hence the ¹⁄₃₂" tick marks are not clearly resolved.

Figure 13:
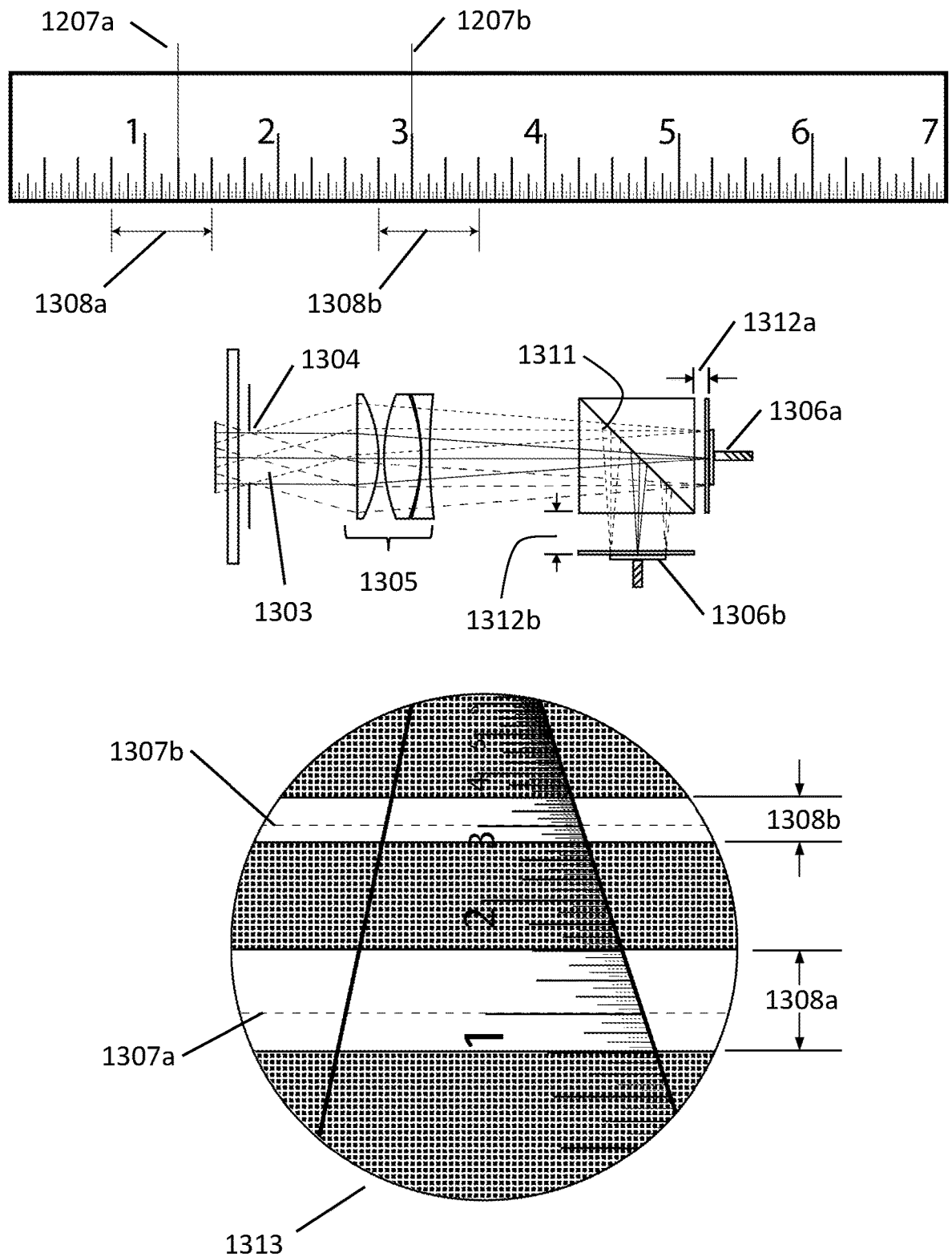
Figure 14:
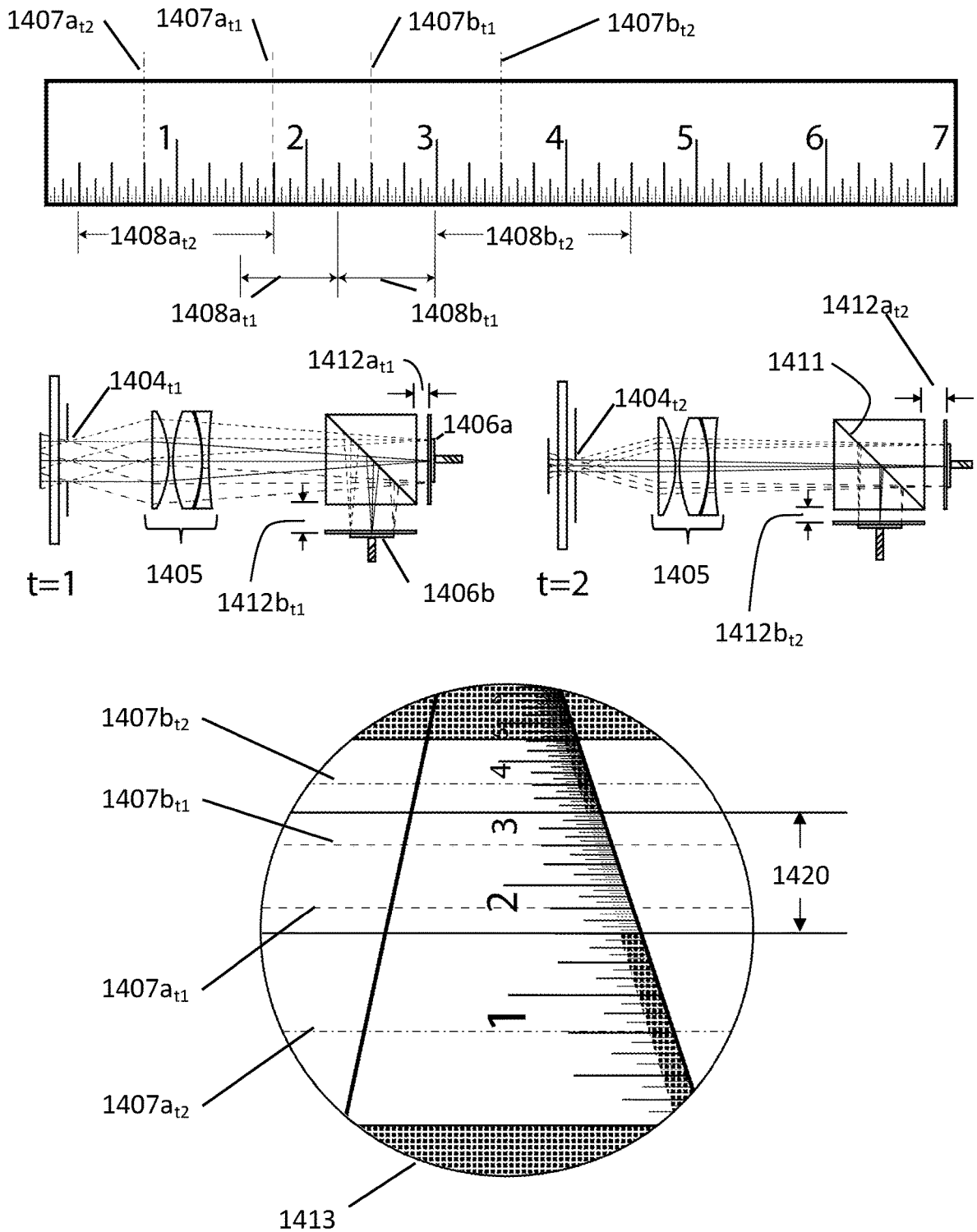
FIG. 14 represents an example mode of the present invention according to FIG. 5 wherein images are collected over two acquisition periods and combined into a final image containing a much wider depth of field and a region of high-resolution.

Of course, there are various possible intermediate modes which may be defined by a user or may be offered as possible pre-existing selections available to the user. These modes may be selected for any number of purposes. One such intermediate example is described with reference to FIG. 13, but it will be known to those skilled in the art that any number of other specialized, selected modes of operation are but obvious variations, and part of the present invention. FIG. 13 represents a selected depth of field mode. In this case imagine an area of interest in the foreground, for example an operation site, and an area of interest in the background, for example the rear most part of the body lumen containing the operation site. In such a case it might be necessary for a high-resolution image of the operation site, and a clear view of the background. For our example, we will assume that the foreground area of interest is located at a depth of 1" and the rearmost part of the body lumen is at 3". In order to obtain a high resolution image of the foreground surgical site, the variable aperture 1304 is opened wide, and the sensors 1306a and 1306b are positioned at different distances 1312a and 1312b respectively. The positions are selected such that the focal plane 1307a of the first detector 1306a is at 1", and the second focal plane 1307b is set at 3" by appropriately positioning the second detector 1306b. The resulting image 1313 comprises two in-focus regions 1308a and 1308b with a non-focused region there between. The planes of interest for a mode of operation such as this could be known a priori and communicated to the imaging device or could be determined in situ by direct measurement, the use of ultra-sound, time of flight, 3D imaging, or other internal measurement techniques known in the art, or a combination of techniques.

A variation on the modes presented thus far involves capturing multiple images from each sensor over a plurality of acquisition periods. This variation allows even more versatility, as the speed and ease with which the aperture diameter may be varied, and/or the sensors repositioned, is utilized to generate images with both high-resolution regions of interest, as well as an extended depth of field. One of many such possible modes, all of which are elements of the present invention, is presented in FIG. 14. In this representative example, images are collected by each sensor at two discrete acquisition periods, one at time t=1 and at time t=2. At time t=1, the aperture 1404 is opened wide, permitting a large beam 1403 to pass there through to the shaping optics 1405. The beam is split by the beamsplitter 1411, and the first image sensor 1406a is spaced a first distance $1412a_{t1}$ from the beamsplitter 1411, and this distance is different from that $1412b_{t1}$ of the second sensor 1406b, defining an in-focus, high resolution region 1420. This first acquisition period, if displayed, would yield a an image similar to that discussed with reference to FIG. 11, that is one with a high resolution over an extended-depth of field. In this case, representing a high resolution region from the 1½" mark to the 3" mark, the remaining view being out of the extended depth-of-field, and therefore out of focus. For the subsequent acquisition period, at time t=2, the variable aperture 1404 will stop down in order to permit the detectors 1406a and 1406b to capture wide depth-of-field images. The detector positions are also be moved between the acquisition at t=1 and t=2 to select new focal planes. Inasmuch as regions between 1½"-3" have already been captured in focus at the first acquisition, the detector distances, $1412a_{t2}$ and $1412b_{t2}$ are be selected such that their respective depths of field $1408a_{t2}$, $1408b_{t2}$ abut or just overlap these regions. In this example, at time t=2, the first detector 1406a has a focal plane $1407a_{t2}$ at ¾", and the second detector 1406b has a focal plane $1407b_{t2}$ at 3½". The four resulting images, collected over two acquisition periods, are processed to produce a resulting image 1413, with an in-focus region from ¼"-4½" and with a high-resolution region 1420 from 1½"-3", where the ¹⁄₃₂" marks are clearly resolved. Outside of this high-resolution region 1420, the ¹⁄₃₂" marks are not clearly resolved. Any optical adjustments necessary to the beam shaping optics can be achieved by methods known in the art in the interval between t=1 and t=2, such as by physically moving the elements of the optical system, or by adjusting a variable liquid lens that may be included as an element thereof. Variations on this mode, generating a resultant image 1413 over more acquisition periods are possible, with the practical limit being that the sum of the time necessary time to collect the images, make adjustments between each collection, and the time necessary to generate and display the image determine the maximum frame rate to be displayed.

Other modes of operation of the present invention are possible that are not particularly related to depth of field. For example High Dynamic Range (HDR) images can be captured with the inventive apparatus, when both of the image sensors are placed at equal distances from the beam splitter, but where the electronic exposure settings of one sensor are different from that of the other. In this example, two images of the same object space are collected, with the same focal plane and depth of field for each detector, but the first sensor collects an image where some elements of the object space are properly exposed and, for example, other elements are under exposed. The second sensor collects an image where the properly exposed elements of the first sensor are over exposed, and the underexposed elements collected by the first sensor are properly exposed. The two collected images are then segmented and recombined by an image processor, by means known in the art, to generate an HDR image which is displayed or stored.

Another benefit conferred by the present invention is the ability to provide automatic selection of optimized modes. The manufacturer of optical devices can take into account various endoscopic conditions, endoscopic optics, measure available light, query the user as to desired output, consider desired frame rates, consider available processing power, and select a "best mode of operation" for the user.

One example of optimization of an endoscopic system according to the present invention is the enabling of the instrument to adjust as appropriate in relation to the digital zoom settings set by the user. For example, a user may select a setting according to that described in FIG. 12 above, being one of moderate resolution and high depth of field. However, during the course of the procedure, the user requires that the image be digitally magnified in order to "zoom in" on an object of interest. At some point in this example, the available resolution of the captured images, as displayed on a monitor, will be reached. That is to say that the resolution of the captured image will match that of the resolution of the output display. Any further digital zoom will result in lower resolution images being displayed. However, according to the present invention, the optical device may appropriately adjust to a higher resolution, lower depth of field mode by opening the variable aperture, and moving one or more of the detectors in order to maintain the desired output resolution.

Another benefit of the present invention is the ability of a universal imaging device, such as a camera head according to the present invention, to be connected to a stock endoscope with an embedded identifier, such as an RFID, optical identifier, electronic or other appropriate identifying means. The camera head reads the identifier, and then selects appropriate setting for the variable aperture and sensor positions, based on the optical properties of the attached endoscope, which are retrieved from a database of known endoscopes by a processing system, such as a Camera Control Unit (CCU) in communication with the camera head, or these parameters could be stored in the endoscope itself and be read by camera head. The CCU will also, in general, contain the image processor used to generate the composite images from those collected by the individual sensors, as discussed above. The variability of the elements of the inventive camera head permits a wide variety of stock endoscopes to be used in conjunction therewith.

It should also be noted that throughout this specification reference has been made to two images sensors being used to generate two differing images of the same scene, however, this should not be considered limiting. Optical designs wherein three or more image sensors are also possible.

The invention being thus described, it will be obvious that the same may be varied in many ways. For instance, capabilities, components or features from each of the optical arrangements above are combinable or transferrable to any of the other optical arrangements disclosed herein. Such variations are not to be regarded as a departure from the spirit and scope of the invention, and all such modifications as would be obvious to one skilled in the art are intended to be included within the scope of the following claims.

What is claimed is:

1. An optical device to be used in conjunction with an image relaying device, such as an endoscope comprising:
    a variable aperture stop through which a beam passes from the image relaying device;
    a lens receiving the first portion of light from the variable aperture stop;
    a beamsplitter receiving the light beam, having passed through the variable aperture and the lens, the beamsplitter separating the light beam into at least a first portion and a second portion;
    a first image sensor receiving the first portion of light, and further comprising a means to adjust the position of the first image sensor parallel to a first optical axis, adjusting, thereby, a first focal plane of a first image captured by the first image sensor;
    a second image sensor receiving the second portion of light, wherein a second image captured by the second image sensor has a second focal plane; and
    an image processor adapted to receive the first and second captured images collected by the image sensors at a first acquisition period and the first and second captured images collected at a subsequent, second acquisition period, and to process at least one of the captured images from the first acquisition period and at least one of the captured images from the second acquisition period into a resulting image having a greater depth of field and/or resolution than any of the individually captured images.

2. The optical device of claim 1, wherein the variable aperture stop is a temporally variable aperture.

3. The optical device of claim 2, wherein captured images from more than two acquisition periods are processed to form the resulting image.

4. The optical device of claim 1, further comprising a means to adjust the position of the second image sensor parallel to a second optical axis, adjusting, thereby, the second focal plane.

5. The optical device of claim 1, wherein the variable aperture stop includes a first diameter defined by the variable aperture stop, wherein an annular polarized filter is disposed in the variable aperture stop defining a second diameter, and wherein the beamsplitter divides the light beam based on polarization.

6. The optical device of claim 1, wherein the lens comprises a liquid lens having a variable curvature or a variable index of refraction.

7. The optical device of claim 1, wherein the lens comprises a movable lens.

8. The optical device of claim 1, wherein captured images from more than two acquisition periods are processed to form the resulting image.

9. The optical device of claim 1, further comprising means by which the optical device can identify the image relaying device.

10. The optical device of claim 9, wherein the means by which the optical device identifies the image relaying device is a radio frequency identification (RFID) reader.

11. The imaging head of claim 10, wherein the imaging processor identifies properties associated with the attached image relaying device based on the detected RFID identifier.

12. The optical device of claim 1, wherein the lens is so configured to result in a telecentric beam being detected by the image sensors.

13. The optical device of claim 1, wherein an electronic exposure setting of the first image sensor is different than the electronic exposure setting of the second image sensor.

14. The optical device of claim 1, wherein the image processor is adapted to process at least three of the captured images to form the resulting image.

15. A method for providing multiple modes of operation by an optical device comprising the steps of
    connecting an image relaying device to the optical device;
    passing a light beam transmitted by the connected image relaying device through a variable aperture stop having an aperture diameter;
    shaping and focusing the light beam passed through the variable aperture with one or more lens elements;
    splitting the light beam into at least a first portion of light and a second portion of light;
    collecting the first portion of light with a first image sensor positioned at a first distance along a first optical path from the beam splitter, the first collected image having a first focal plane;
    collecting the second portion of light with a second image sensor positioned at a second distance along a second optical path from the beam splitter, the second collected image having a second focal plane;

defining a first mode of operation as that wherein images are captured by the image sensors according to their present positioning and the present diameter of the variable aperture;

adjusting one or more of
the aperture diameter of the variable aperture stop;
the position or curvature of one or more of the lens elements;
the position of the first image sensor; or
the position of the second image sensor;

defining a second mode of operation as that wherein images are captured by the image sensors after the adjustment step;

collecting image light from the first and second image sensors in the first mode at a first acquisition period;

collecting image light from the first and second image sensors in the second mode at a subsequent second acquisition period; and processing at least one of the captured images from the first acquisition period and at least one of the captured images from the subsequent, second acquisition period into a resulting image having a greater depth of field and/or resolution than any of the individually captured images.

16. The method of claim 15, wherein the step of adjusting the position of the first image sensor comprises adjusting its position along a first optical axis, changing, thereby, the focal plane of the image collected by the first image sensor.

17. The method of claim 15, wherein the step of shaping and focusing the light beam results in a telecentric ray bundle being detected by the image sensors.

18. The method of claim 15, wherein the step of connecting the image relaying device comprises the further step of detecting an identifying signal from an identifier located on the image relaying device.

19. The method of claim 18, comprising the further step of determining optical properties of the attached, identified image relaying system, and selecting a mode of operation compatible with the determined optical properties of the relaying system.

20. The method of claim 15, wherein the first and second modes of operation are automatically selected based on the resolution requirements of a user, the automatic selection comprising the steps of
determining the minimum resolution required by the user; and
selecting the appropriate modes by adjusting the image sensor positions and/or the aperture diameter and/or lens position or curvature, such that the resulting image is of at least this minimum resolution required.

21. The method of claim 20, wherein the step of automatically selecting the modes of operation as a third mode for use with a digital zoom, wherein, in the first mode a displayed image, prior to the digital zoom, is at a resolution greater than the minimum required resolution, and wherein the user is permitted to select a digital zoom option, and wherein the resulting digitally zoomed image would be displayed at a resolution less than the minimum required resolution, comprising the further step of selecting the second mode such that the resulting image is displayed at least of the minimum resolution required.

22. The method of claim 15, wherein
the step of adjusting the sensor position, the lens position or curvature, or the aperture diameter comprises the further steps of
adjusting the positions of the image sensors such that both image sensors view the same focal plane; and
adjusting an electronic exposure setting on at least one of the sensors such that the electronic exposure setting of the first sensor is different than the electronic exposure setting of the second sensor; and
wherein the second image is processed from the two differently exposed images to form a resultant image with a higher dynamic range than either the first or second individually captured images.

23. The method of claim 15, wherein the step of processing the captured images includes processing at least three of the captured images to form the resulting image.

24. An optical device to be used in conjunction with an image relaying device, such as an endoscope comprising:
a variable aperture stop through which a beam passes from the image relaying device;
a lens receiving the first portion of light from the variable aperture stop;
a beamsplitter receiving the light beam, having passed through the variable aperture and the lens, the beamsplitter separating the light beam into at least a first portion and a second portion;
a first image sensor receiving the first portion of light, and further comprising a means to adjust the position of the first image sensor parallel to a first optical axis, adjusting, thereby, a first focal plane of a first image captured by the first image sensor;
a second image sensor receiving the second portion of light, wherein a second image captured by the second image sensor has a second focal plane; and
an image processor that processes the collected images into a resulting image having a greater depth of field and/or resolution than either the first or second individually captured image,
wherein an electronic exposure setting of the first image sensor is different than the electronic exposure setting of the second image sensor.

* * * * *